United States Patent
Greenfield et al.

(10) Patent No.: US 7,470,519 B2
(45) Date of Patent: Dec. 30, 2008

(54) METHODS FOR DETECTING TAFIA OR TAFIAI

(75) Inventors: Robert S. Greenfield, Trumbull, CT (US); Seong Soo A. An, Hopewell Junction, NY (US)

(73) Assignee: American Diagnostica, Inc., Stamford, CT (US)

( * ) Notice: Subject to any disclaimer, the term of this patent is extended or adjusted under 35 U.S.C. 154(b) by 0 days.

(21) Appl. No.: 10/526,167

(22) PCT Filed: Aug. 29, 2003

(86) PCT No.: PCT/US03/27061

§ 371 (c)(1),
(2), (4) Date: Feb. 8, 2006

(87) PCT Pub. No.: WO2004/020976

PCT Pub. Date: Mar. 11, 2004

(65) Prior Publication Data

US 2006/0183172 A1  Aug. 17, 2006

Related U.S. Application Data

(60) Provisional application No. 60/406,756, filed on Aug. 29, 2002.

(51) Int. Cl.
*G01N 33/53* (2006.01)
(52) U.S. Cl. .......................... 435/7.71; 435/13; 435/7.1
(58) Field of Classification Search .................. None
See application file for complete search history.

(56) References Cited

U.S. PATENT DOCUMENTS

| | | | |
|---|---|---|---|
| 5,206,161 A | 4/1993 | Drayna et al. |
| 5,364,934 A | 11/1994 | Drayna et al. |
| 5,474,901 A | 12/1995 | Drayna et al. |
| 5,593,674 A | 1/1997 | Drayna et al. |
| 5,952,305 A | 9/1999 | Pfeffer et al. |
| 5,985,562 A | 11/1999 | Morser et al. |
| 5,993,815 A | 11/1999 | Bajzar et al. |
| 2002/0177560 A1 | 11/2002 | Greenfiled et al. |

FOREIGN PATENT DOCUMENTS

| FR | 2826962 | 1/2003 |
|---|---|---|
| WO | WO 98/55645 | 12/1998 |
| WO | WO 99/20260 | 4/1999 |

OTHER PUBLICATIONS

Nagashima et al. (Thrombosis Research, vol. 981, pp. 333-342, May 2000.*
Bouma et al., 1999, "Factor XI Dependent and Independent Activation of Thrombin Activatable Fibrinolysis Inhibitor (TAFI) in Plasma Associated with Clot Formation," *Thromb. Haemost.* 82(6):1703-1708.
Schatteman et al., 1999, "Assay of Procarboxypeptidase U, a Novel Determinant of the Fibrinolytic Cascade, in Human Plasma," *Clinical Chemistry* 45(6):807-813.
Schneider et al., 2001, "Paradoxical Attenuation of Fibrinolysis by Reversible Inhibitors of TAFIa," *Blood* 98(11):254a.
Antovic et al., 2001, Total thrombin-activatable fibrinolysis inhibitor (TAFI) antigen and pro-TAFI in patients with haemophilia A,: *Haemophilia* 7:557-560.
Bajzar et al., 1995, "Purification and characterization of TAFI, a thrombin-activable fibrinolysis inhibitor", J. Biol. Chem. 270(24):14477-14484.
Boffa et al., 1998, "Plasma and recombinant thrombin-activable fibrinolysis inhibitor (TAFI) and activated TAFI compared with respect to glycosylation, thrombin/thrombomodulin-dependent activation, thermal stability, and enzymatic properties", J. Biol. Chem. 273(4):2127-2135.
Boffa et al., 2000, "Roles of thermal instability and proteolytic cleavage in regulation of activated thrombin-activable fibrinolysis inhibitor", J. Biol. Chem. 275(17):12868-12878.
Boffa et al., 2001, "Thrombin Activatable Fibrinolysis Inhibitor (TAFI): Molecular Genetics of an Emerging Potential Risk Factor for Thrombotic Disorders", Current Drug Targets 1:59-74.
Bouma et al., 2001, "Thrombin-Activatable Fibrinolysis Inhibitor (TAFI, Plasma Procarboxypeptidase B, Procarboxypeptidase R, Procarboxypeptidase U)", Thrombosis Research 101:329-354.
Fava et al., 1994, "Vascular permeability factor/endothelial growth factor (VPF/VEGF): accumulation and expression in human synovial fluids and rheumatoid synovial tissue", J. Exp. Med. 180:341-346.
Hendriks et al., 1990, "Purification and characterization of a new arginine carboxypeptidase in human serum", Biochim. Biophys. Acta 1034:86-92.

(Continued)

*Primary Examiner*—Hope A Robinson
(74) *Attorney, Agent, or Firm*—Jones Day (57) ABSTRACT

The invention relates to a diagnostic assay for selectively measuring levels of the 35kD form of thrombin-activatable fibrinolysis inhibitor (TAFIa or TAFIai), or a derivative or variant thereof, but not the TAFI proenzyme (TAFI) or the N-terminal activation peptide of TAFI.

32 Claims, 6 Drawing Sheets

OTHER PUBLICATIONS

Klement et al., 1999, "A Novel Approach to Arterial Thrombolysis", Blood 94(8):2735-2743.

Marx et al., Dec. 1-5, 2000, 42nd Annual Meeting of the American Society of Hematology, San Francisco, CA (Database Accession No. PREV200100311714).

Mosnier et al., 2001, "Protein C inhibitor regulates the thrombin-thrombomodulin complex in the up- and down regulation of TAFI activation", Thromb. Haemost. 86:1057-1064.

Mosnier et al., 2001, "The defective down regulation of fibrinolysis in haemophilia A can be restored by increasing the TAFI plasma concentration", Thromb. Haemost. 86:1035-1039.

Mosnier et al., 2001, "The role of protein S in the activation of thrombin activatable fibrinolysis inhibitor (TAFI) and regulation of fibrinolysis", Thromb. Haemost. 86:1040-1046.

Seong et al., Dec. 1-5, 2000, 42nd Annual Meeting of the American Society of Hematology, San Francisco, CA (Database Accession No. PREV200100308410).

Sumii et al., 2002, "Involvement of matrix metalloproteinase in thrombolysis-associated hemorrhagic transformation after embolic focal ischemia in rats", Stroke 33:831-836.

Taylor et al., 1985, "Whole blood clot lysis: in vitro modulation by activated protein C", Thromb. Res. 37:639-649.

Wang et al., 1994, "Carboxypeptidase U, a plasma carboxypeptidase with high affinity for plasminogen", J. Biol. Chem. 269(22):15937-15944.

* cited by examiner

METHODS FOR DETECTING TAFIA OR TAFIAI

This application is a U.S. national stage application under 35 U.S.C. § 371 of PCT/US03/27061, filed Aug. 29, 2003 and claims the benefit under 35 U.S.C. § 119(e) of U.S. provisional application No. 60/406,756, filed Aug. 29, 2002, which is incorporated by reference herein in its entirety.

1 FIELD OF THE INVENTION

The invention relates to a diagnostic assay for selectively measuring levels of the 35 kD form of thrombin-activatable fibrinolysis inhibitor (TAFIa or TAFIai), or a derivative or variant thereof, but not the TAFI proenzyme (TAFI) or N-terminal activation peptide of TAFI.

2 BACKGROUND OF THE INVENTION

A proper balance between the activities of coagulation and fibrinolytic cascades is needed both to protect an organism from excessive blood loss upon injury and to maintain blood flow within the vascular system. The two opposing coagulation and fibrinolytic cascades are recognized to comprise a series of zymogen to enzyme conversions which termninate in the two respective proteolytic enzymes, thrombin and plasmin. These enzymes catalyze the formation and removal of fibrin within the circulatory system. Imbalances are characterized by either bleeding or thrombotic tendencies which may result in heart attacks or strokes in the organism.

Thrombin activatable fibrinolytic inhibitor (TAFI) is a 60 kD glycoprotein present in human plasma that modulates fibrinolyisis in vivo. TAFI present in plasma is a proenzyme form which is most efficiently activated by proteolytic cleavage at Arg-92 with a thrombin-thrombomodulin complex. The proenzyme form of TAFI may also be activated by proteolytic cleavage by other proteolytic enzymes including, but not limited to, thrombin or plasmin. Upon activation of the TAFI proenzyme by proteolytic cleavage with thrombin-thrombomodulin, an active enzyme of 35 kD is formed with carboxypeptidase-like activity (TAFIa). This molecule has also been referred to in the literature as plasma carboxypeptidase B (PCPB), or plasma carboxypeptidase U (PCPU). TAFIa rapidly loses enzymatic activity through a temperature-dependent ($t_{1/2}$=10 min at 37° C.) inactivation process. The inactivation of TAFIa is not due to a proteolytic process, but rather to a conformational change in the protein structure which can be followed by a change in the fluorescence spectrum of the protein. The inactivated TAFIa enzyme is referred to as TAFIai (35 kD). The spontaneous temperature-dependent inactivation of TAFIa to TAFIai is believed to be the major mechanism by which TAFIa activity is modulated during fibrinolysis.

Modulation of fibrinolysis occurs when TAFIa cleaves C-terminal arginine and lysine residues of partially degraded fibrin, thereby inhibiting the stimulation of tissue plasminogen activator (t-PA) modulated plasminogen activation. The fibrinolytic system is activated primarily by t-PA which is provided by damaged cells in the blood vessel wall. t-PA converts circulating plasminogen to the active protease plasmin and can produce either slow enhancement of fibrinolysis or, when combined with fibrin, rapid enhancement of fibrinolysis. The effect of t-PA on fibrinolysis can be blocked by a class of inhibitors termed plasminogen activator inhibitors (PAIs), of which several have been identified.

Thrombomodulin is a component of the blood vessel wall which binds thrombin and changes its specificity from fibrinogen to protein C, resulting in a molecule possessing anticoagulant, rather than procoagulant, activity. The thrombin-thrombomodulin complex catalyzes cleavage of protein C to activated protein C, which results in down-regulation of the coagulation cascade by proteolytically inactivating the essential co-factors, Factor Va and VIIIa. In this manner, the body regulates coagulation cascade.

Studies such as that by Taylor et al., *Thromb. Res.* 37:639 (1985) have suggested that activated protein C is not only an anticoagulant, but also profibrinolytic, both in vivo and in vitro. Subsequently, it was determined that protein C only appears profibrinolytic because it prevents the thrombin-catalyzed activation of a previously unknown fibrinolysis inhibitor, whose precursor was isolated from plasma and designated as being TAFI.

TAFI was discovered independently in three different laboratories. In initially appeared as an unstable carboxypeptidase B-like molecule in human serum and was described by Hendriks et al., *Biochim. Biophys. Acta* 1034:86 (1990). A year later the cDNA for the molecule was cloned, its amino acid sequence was described, its activation by trypsin and its enzymatic properties toward synthetic carboxypeptidase B substrates was reported (see U.S. Pat. No. 5,206,161). In 1994, Wang et al., (*J. Biol. Chem.* 269:15937 (1994)) isolated the activated molecule and named it carboxypeptidase U ("U" being designated for unstable). Subsequently, Nesheim et al. (*J Biol. Chem.* 270:14477 (1995)) showed that the protein was both activated by thrombin and inhibits fibrinolysis, and designated the molecule TAFI. The co-identity of PCPB, PCPU, and TAFI has been established by their independent chromatographic behavior on plasminogen Sepharose® and the amino acid sequences present at the activation cleavage site.

Figure 1:
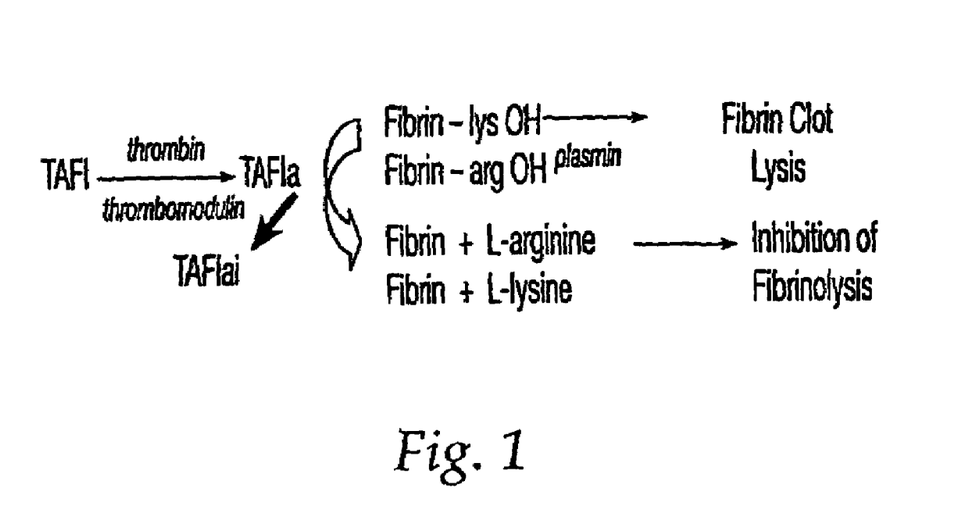
FIG. 1 is a schematic illustration of the mechanism of TAFI inhibition of fibrinolysis.

The mechanism of TAFI inhibition of fibrinolysis can be schematically described as depicted in FIG. 1.

The conversion of TAFI to TAFIa and subsequently to TAFIai indicates an ongoing fibrinolytic process. Therefore, the presence of TAFIa and TAFIai in plasma is a marker of the fibrinolytic process. Alterations of TAFI levels have been identified in a number of pathological conditions including vascular and heart diseases, liver disease, hemophilia, cancer, leukemia and stroke. Therefore, accurate quantitation of TAFI, TAFIa and TAFIai levels in plasma provides information in the understanding and diagnosis of many diseases in which fibrinolysis plays a role.

Several ELISAs (enzyme linked immunosorbent assay) are commercially available which are designed to measure the total level of all forms of TAFI in plasma (e.g., Imuclone TAFI 873 by American Diagnostica, Inc.; TAFI ELISA by Affinity Biologicals). An ELISA has been reported which only measures the 60 kD TAFI proenzyme (Stromquist et al. *Thromb. Hemost.* 85:12-17 (2001)). A chromogenic assay based upon a functional assay is commercially available which only measures the 60 kD proenzyme form of TAFI (Actichrome 874 by American Diagnostica, Inc.).

The 60 kD proenzyme form of TAFI shares common antigenic epitopes with TAFIa and TAFIai. There have not been any antibodies described which have are specific for TAFIa and TAFIai but not the 60 kD proenzyme form of TAFI. Accordingly, an ELISA that specifically measures TAFIa and TAFIai in the presence of the 60 kD proenzyme form of TAFI has not been developed.

Diagnostic assays selective for TAFIa and TAFIai in the presence of the 60 kD proenzyme form of TAFI would be useful for identifying and monitoring changes in the fibrinolytic process. Such changes are indicative of diseases where the fibrinolytic process is involved, such as vascular and heart diseases, liver disease, hemophilia, cancer, leukemia and stroke. Accordingly, there is a need in the art for effective assays selective for TAFIa and TAFIai levels in the presence of the 60 kD proenzyme form of TAFI.

Citation or identification of any reference in this section is not to be construed as such reference being prior art to the present application.

3 SUMMARY OF THE INVENTION

The present invention is based in part on the discovery that potato carboxypeptidase inhibitor (PTCI) binds to both TAFIa and TAFIai but not to the 60 kD proenzyme form of TAFI nor to the N-terminal activation peptide of TAFI. In brief, the invention is directed to an assay useful for measuring TAFIa or TAFIai (or a derivative or variant thereof) levels comprising detecting a complex comprised of a specific binding moiety (such as, but not limited to, PTCI) for TAFIa or TAFIai and the TAFIa or TAFIai protein (or a derivative or variant thereof). In one embodiment, the assay is useful for specifically measuring TAFIa or TAFIai levels (i.e., detecting the TAFIa and/or TAFIai forms of TAFI but not detecting the 60 kD pro-enzyme form or the N-terminal activation peptide of TAFI) in a sample also containing (or potentially containing) the 60 kD proenzyme form of TAFI and/or the N-terminal activation peptide of TAFI where the binding moiety is PTCI. In a particular embodiment, the TAFIa/PTCI complex or the TAFIai / PTCI complex is detected with an anti-TAFI antibody.

In a preferred embodiment, the present invention is directed to an enzyme linked immunosorbent (ELISA)-like assay useful for measuring TAFIa or TAFIai (or a derivative or variant thereof) protein (antigen) levels in solutions which may or may not contain the 60 kD proenzyme form of TAFI or the N-terminal activation peptide of TAFI. The assay is useful for diagnostic purposes related to the measurement of TAFIa and TAFIai levels.

The present invention is also directed to a method of assaying biological solutions including, but not limited to, blood, plasma, urine, serum, semen and cerebral or spinal fluid for TAFIa or TAFIai (or a derivative or variant thereof) levels. The assay can be used to diagnose a patient as having a particular disease or disorder related to altered levels of TAFIa or TAFIai or altered levels of TAFIa or TAFIai activity or to monitor a patient that has been previously diagnosed with such a disease or disorder. The assay can be further used to monitor a patient receiving treatment for a particular disease or disorder related to altered TAFIa or TAFIai levels or activity and/or to monitor a patient receiving treatment that alters TAFIa or TAFIai levels or activity. In certain embodiments, the treatment is anti-coagulant therapy. In other embodiments, the treatment is pro-coagulant therapy. In other embodiments, the treatment is anti-fibrinolytic or pro-fibrinolytic.

In one embodiment, the patient has or is susceptible to having a hemorrhagic disease or disorder. In a particular embodiment, the hemorrhagic disease or disorder is associated with a hyperfibrinolytic state. In a specific embodiment, the hyperfibrinolytic state is hemophilia A or hemophilia B.

In another embodiment, the patient has or is susceptible (i.e., has a predisposition caused by genetic or environmental factors or by virtue of having a certain disease, disorder or condition associated therewith, or from undergoing or having undergone therapy that can result therein) to having bleeding side-effects associated with the administration of tissue plasminogen activator (t-PA), or an analog thereof, aspirin (particularly an overdose of aspirin) and/or other anti-coagulants.

In another embodiment, the patient has or is susceptible to having a thrombotic disease or disorder.

In another embodiment, the patient has or is susceptible to having cancer.

In another embodiment, the patient has or is susceptible to having a liver disease.

In another embodiment, the patient will be undergoing, is undergoing or has undergone surgery. In particular embodiment, the surgery is an organ transplant. In another particular embodiment, the surgery is cardiovascular.

In another embodiment, the invention is directed to a kit comprising the components of the TAFIa/TAFIai assay (i.e., PTCI, TAFIa/TAFIai standard, agent capable of binding to TAFIa/PTCI complex or TAFIai/PTCI complex, a substrate of said agent, buffer, quenching reagent).

These and other aspects of this invention will be evident upon reference to the following detailed description and figures. To that end, certain patent and other documents are cited herein to more specifically set forth various aspects of this invention. Each of these documents are hereby incorporated by reference herein in its entirety. Citation of the references herein is in no way an admission that they constitute prior art.

3.1 Definitions

The terms "analog", "polymorphism" and "variant" as used herein refers to a polypeptide that possesses a similar or identical function as a particular protein (e.g., TAFI, TAFIa or TAFIai), or a fragment thereof, but does not necessarily comprise a similar or identical amino acid sequence or structure of that protein complex or a fragment thereof. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of the protein or protein complex or a fragment thereof as described herein (e.g., human or murine TAFI, TAFIa or TAFIai); (b) a polypeptide encoded by a nucleotide sequence that hybridizes under stringent conditions to a nucleotide sequence encoding a protein or protein complex of the invention, or fragment thereof, as described herein of at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the protein or protein complex of the invention or a fragment thereof as described herein. A polypeptide with similar structure to a protein or protein complex of the invention or a fragment thereof as described herein refers to a polypeptide that has a similar secondary, tertiary or quaternary structure of said protein or protein complex or a fragment thereof as described herein. The structure of a polypeptide can be determined by methods known to those skilled in the art, including but not limited to, X-ray crystallography, nuclear magnetic resonance, and crystallographic electron microscopy.

The term "binding moiety" as used herein refers to a chemical or biological substance capable of specifically binding to or specifically being bound by TAFIa or TAFIai (i.e., a non-specific protein or other moiety does not significantly compete for binding with a specific moiety). Such chemical or biological substances include, but are not limited to, low molecular weight inhibitors of TAFIa or TAFIai, peptides, small proteins, plasminogen and PTCI.

The term "derivative" as used herein refers to a polypeptide that comprises an amino acid sequence of a protein (e.g., TAFI, TAFIa or TAFIai) or protein complex of the invention or a fragment thereof as described herein that has been altered by the introduction of amino acid residue substitutions, deletions or additions. The term "derivative" as used herein also refers to a protein or protein complex of the invention or a fragment thereof that has been modified, i.e., by the covalent attachment of any type of molecule to the polypeptide. For example, but not by way of limitation, a protein or protein complex or a fragment thereof may be modified, e.g., by glycosylation, acetylation, pegylation, phosphorylation, amidation, derivatization by known protecting/blocking groups, proteolytic cleavage, linkage to a cellular ligand or other protein, etc. A derivative of a protein or protein complex or a fragment thereof may be modified by chemical modifications using techniques known to those of skill in the art, including, but not limited to specific chemical cleavage, acetylation, formylation, or metabolic synthesis of tunicamycin. Further, a derivative of a protein or protein complex or a fragment thereof may contain one or more non-classical amino acids. A polypeptide derivative possesses a similar or identical function as a protein or protein complex or a fragment thereof described herein.

The phrases "TAFIa/PTCI complex", "TAFIai/PTCI complex" or "TAFIa or TAFIai/PTCI complex" mean a complex formed between either TAFIa and PTCI or TAFIai and PTCI.

The phrase "modulation of fibrinolysis" means the inhibition, reduction, enhancement or activation of the fibrinolytic cascade which may have an anti-coagulant or procoagulant effect. "TAFIa inhibitor" or "inhibitors of TAFIa" means any molecule that blocks, reduces or retards the cleavage of fibrin or other substrates by TAFIa.

The term "prophylactic agent" means an agent capable of preventing or reducing the risks, incidence or recurrence of a disease or disorder in a patient. In one embodiment, the prophylactic agent is one which is capable of preventing a hemorrhagic or thrombotic disorder.

The term "therapeutic agent" means an agent capable of modifying, controlling, delaying or reversing a disease or disorder or ameliorating the symptoms of a disease or disorder in a patient. In one embodiment, the therapeutic agent is one which is capable of modifying, controlling, delaying, reversing or ameliorating the symptoms of a hemorrhagic or thrombotic disorder.

The terms "subject" and "patient" refer to a mammal such as a non-primate (e.g., cows, pigs, horses, cats, dogs, mice, rats etc.) or a primate (e.g., monkeys and humans). Preferably the subject or patient is a mammal, more preferably, a human.

The terms "prevent", "preventing" and "prevention" refer to the prevention of the recurrence, spread or onset of the hemorrhagic or thrombotic disease or disorder, or symptoms associated with the disease or disorder, in a patient by the administration of a prophylactic or therapeutic agent.

The terms "treat", "treating" and "treatment" refer to the, modification, control, reversal or amelioration of the symptoms of a hemorrhagic or thrombotic disease or disorder. In certain embodiments, such terms refer to the minimizing or delay of the hemorrhagic or thrombotic disease or disorder.

The phrase "in combination" refers to the use of more than one prophylactic and/or therapeutic agents to treat, prevent or manage a hemorrhagic or thrombotic disease or disorder. The prophylactic or therapeutic agents of the combination therapies of the present invention can be administered concomitantly or sequentially. The prophylactic or therapeutic agents of the combination therapies of the present invention also can be cyclically administered. Cycling therapy involves the administration of a first agent for a period of time, followed by the administration of a second agent for a period of time and repeating this sequential administration, i.e., the cycle, in order to reduce the development of resistance to one of the therapies, to avoid or reduce the side effects to one of the therapies, and/or to improve the efficacy of the treatment.

The terms "manage", "managing" and "management" refer to the beneficial effects that a patient derives from a prophylactic or therapeutic agent, which does not result in a cure of the disorder. In certain embodiments, a patient is administered one or more prophylactic or therapeutic agents to "manage" a disease or disorder, or symptoms associated with the disease or disorder, so as to prevent the progression or worsening of the disease or disorder.

The term "t-PA" refers to native t-PA and recombinant t-PA as well as homologs, derivatives and polymorphisms of t-PA that retain the catalytic activity of native t-PA.

The phrases "specifically binds TAFIa or TAFIai" or "binds specifically TAFIa or TAFIai" as used to describe to a chemically or biological moiety mean that the chemical or biological moiety binds or is bound by no more than 10%, more preferably no more than 5%, more preferably no more than 2%, more preferably no more than 1%, more preferably no more than 0.5%, more preferably no more than 0.1%, more preferably no more than 0.01% and most preferably no more than an undetectable amount in the particular assay being used, of the 60 kD proenzyme form of TAFI or the N-terminal activation peptide of TAFI.

The phrase "specifically measuring the level of TAFIa or TAFIai" means detecting the amount of TAFIa or TAFIai in a sample without detecting a significant amount (e.g., no more than 10%, more preferably no more than 5%, more preferably no more than 2%, more preferably no more than 1%, more preferably no more than 0.5%, more preferably no more than 0.1%, more preferably no more than 0.01% of the amount present in the sample) of 60 kD proenzyme form of TAFI or the N-terminal activation peptide of TAFI.

The phrase "stabilized TAFIa" means TAFIa that has a half-life of at least one hour at room temperature, more preferably of at least two hours, more preferably of at least four hours, more preferably of at least eight hours, more preferably of at least twelve hours, more preferably of at least twenty-four hours and most preferably of at least forty-eight hours, all at room temperature.

4 BRIEF DESCRIPTION OF THE FIGURES

FIG. 1.

FIG. 2.

FIG. 3.

FIG. 4.

FIG. 5.

FIG. 6.

5 DETAILED DESCRIPTION OF THE INVENTION

5.1 TAFIa/TAFIai Specific Assay

The present invention is directed to an assay useful for measuring TAFIa or TAFIai (or a derivative or variant thereof) levels in a sample, which may or may not contain the 60 kD proenzyme form of TAFI or the N-terminal activation peptide of TAFI, to detect TAFIa and TAFIai but not the 60 kD proenzyme form of TAFI or the N-terminal activation peptide of TAFI. The present invention is based in part on the discovery that potato carboxypeptidase inhibitor (PTCI) is capable of binding to TAFIai as well as TAFIa but not to the 60 kD proenzyme form of TAFI nor to the N-terminal activation peptide of TAFI. The assay is useful for diagnostic purposes related to the specific measurement of TAFIa and TAFIai (or a derivative or variant thereof) levels, but not levels of the 60 kD pro-enzyme form or the N-terminal activation peptide of TAFI, in a sample which may or may not contain the 60 kD proenzyme form of TAFI or the N-terminal activation peptide of TAFI.

In a preferred embodiment, the assay measures the level of TAFIa and TAFIai in a solution. Preferably, the assay is used to measure the level of TAFIa and TAFIai in a biological solution (e.g., blood, plasma, urine, serum, semen and cerebral or spinal fluid). The assay may also be used to quantify TAFIa and TAFIai levels in tissue samples as well as purified enzymatic systems and cell culture fluids.

In certain embodiments, the invention is directed to any assay using a binding moiety which specifically binds TAFIa and/or TAFIai, but not the 60 kD proenzyme form of TAFI or the N-terminal activation peptide of TAFI, and wherein the TAFIa/binding moiety complex or, TAFIai/binding moiety complex is then detected. In one embodiment, the binding moiety is a low molecular weight inhibitor. In another embodiment, the binding moiety is a small protein. In another embodiment, the binding moiety is plasminogen. In another embodiment, the binding moiety is a TAFIa or TAFIai specific antibody. In a preferred embodiment, the binding moiety is PTCI or a derivative or analog thereof.

Complex formation is either detected directly, i.e., where the binding moiety is detectably labeled (e.g., a calorimetric, fluorescent, chemiluminescent, enzyme, radioactive or magnetic label), or by a reagent that binds the complex, said reagent being detectably labeled.

The methods of the present invention can be applied to any assay format known in the art, or variations thereof. In one embodiment, the assay is an antibody-based immunoassay, wherein proteins interact with TAFIa or TAFIai or a TAFIa or TAFIai/binding moiety complex. Immunoassays for detecting antigen are well known in the art, and involve the formation of antigen-antibody complexes. The antigen may be added in liquid form, as is performed on immunodiffusion plates, or immobilized on a surface, as is performed using an enzyme-linked immunosorbent assay ("ELISA") in the popular 96-well format. In an immunodiffusion assay, the antibody-antigen complex can be detected as a precipitation line. In a radioimmunoassay ("RIA"), a radioactive isotope is used to detect the presence of the antigen. In an enzyme immunoassay, a detectable marker produced by enzymatic activity (upon a chromogenic, fluorogenic or radioactive substrate, for example) is used to detect the presence of the antigen (Engvall and Perlmann, 1972, "Enzyme-linked immunosorbent assay, Elisa. 3. Quantitation of specific antibodies by enzyme-labeled anti-immunoglobulin in antigen-coated tubes" J. Immunol. 109:129-35). In a preferred embodiment, the antibody used in the immunoassay specifically binds to TAFIa or TAFIai and binds no more than 10%, more preferably no more than 5%, more preferably no more than 2%, more preferably no more than 1%, more preferably no more than 0.5%, more preferably no more than 0.1%, more preferably no more than 0.01% and most preferably no more than an undetectable amount (i.e., undetectable in the particular assay method) of the 60 kD proenzyme form of TAFI or the N-terminal activation peptide of TAFI. Alternatively, such an immunoassay is used to detect a TAFIa or TAFIai/binding moiety complex. For example, an antibody that recognizes TAFIa or TAFIai (and may also recognize the 60 kD proenzyme form of TAFI when the complex has been isolated from the sample) is used.

One type of immunoassay is the "sandwich" technique. Sandwich assays commonly use an ELISA readout and involve the use of at least two antibodies. Typically, a sample potentially containing the antigen of interest is contacted with a first antibody on a solid support. After removing unbound sample (e.g., 60 kD proenzyme form of TAFI or the N-terminal activation peptide of TAFI), a second, enzyme-conjugated antibody is contacted with the antigen bound to the first antibody. After removal of unbound second antibody, a substrate (e.g., colorimetric, fluorescent, chemiluminescent, enzyme, radioactive or magnetic) of the enzyme is contacted with the antibody-antigen-antibody complex on the solid support. Production of a detectable marker indicates presence of the antigen in the sample, and the amount of detectable marker produced or the rate of production of a detectable marker can be used to determine the quantity of the antigen. In this embodiment, the antibody or other binding moiety on the solid support binds specifically to TAFIa or TAFIai. The second antibody does not necessarily need to bind specifically to TAFIa or TAFIai because a washing step will remove any unbound protein prior to the addition of the second antibody.

In one variation of the sandwich technique, a non-antibody moiety that specifically binds to or is specifically bound by TAFIa or TAFIai is immobilized on a solid support. In one embodiment, the assay comprises PTCI that is immobilized on a solid support. In another embodiment, the assay comprises a low molecular weight inhibitor, a small protein or plasminogen immobilized on a solid support. In a particular embodiment, the solid support is a microtiter plate or microwell strip. In embodiments wherein an ELISA assay format is used, a standard ELISA plate reader can be used to analyze the results of the assay and to quantitate the amount of TAFIa or TAFIai present in the sample.

In another embodiment, the solid support used in the assay is a bead or microparticle. In this embodiment, an antibody or other moiety that specifically binds to or is specifically bound by TAFIa or TAFIai is immobilized on the bead or microparticle. In a certain embodiment the bead or microparticle is in a suspension (e.g., for use in flow cytometry or a cytometric assay). The interaction between TAFIa or TAFIai and the antibody or other moiety that specifically binds to or is specifically bound by TAFIa or TAFIai is then detected, or the beads with TAFIa or TAFIai bound are quantitated. Such detection methods are well-known in the art. In specific embodiments, the bead or microparticle can be polystyrene, acrylic, magnetic, dyed, carboxylate modified or streptavidin modified.

In another embodiment, the solid support is a biochip or microarray. In this embodiment, the antibody or other moiety that specifically binds to or is specifically bound by TAFIa or TAFIai is immobilized on a biochip or microarray and the binding of TAFIa or TAFIai is subsequently detected.

In another embodiment, the assay comprises using PTCI to detect TAFIa or TAFIai in a gel or TAFIa or TAFIai that has been resolved by electrophoresis (e.g., Western blot analysis, PAGE or SDS-PAGE).

In one embodiment, the assay comprises PTCI that is free in solution. In a particular embodiment, the assay comprises PTCI that is free in solution to detect TAFIa or TAFIai that is immobilized on a solid support. In this embodiment, the TAFIa or TAFIai can be immobilized on a 96-well plate such as in an ELISA assay, on a bead or microparticle, or on a biochip as in the assay formats discussed above.

In a further embodiment, the assay comprises the use of an agent capable of binding to or being bound by a TAFIa or TAFIai/PTCI complex. It is not necessary that this agent be specific for TAFIa or TAFIai if a washing step has been performed after the formation of the TAFIa or TAFIai/PTCI complex. However, if the protocol of the particular assay being used allows for other forms of TAFI (e.g., the 60 kD proenzyme form) to be present, it is preferred that the agent be specific for TAFIa or TAFIai/PTCI complex. In particular, this agent is any moiety that binds to or is bound by a TAFIa/PTCI complex or binds to or is bound by a TAFIai/PTCI complex. In one embodiment, the agent binds to the TAFIa or TAFIai region of the TAFIa or TAFIai/PTCI complex. In another embodiment, the agent binds to a PTCI region of the TAFIa or TAFIai/PTCI complex, but preferably does not bind to free PTCI, unless free PTCI has been removed prior to addition of the moiety that binds to the TAFIa/PTCI complex or TAFIai/PTCI complex. In another embodiment, the agent binds to both the TAFIa or TAFIai region and the PTCI region of the TAFIa or TAFIai/PTCI complex. In a preferred embodiment, the agent is an antibody that binds to TAFIa and/or TAFIai. In one embodiment, the agent (e.g., antibody) is labeled so that its presence is detectable (e.g., such as a colorimetric, fluorescent, chemiluminescent, enzyme, radioactive or magnetic label). In a preferred embodiment, the anti-TAFIa or anti-TAFIai antibody is conjugated to an enzyme, to another antibody or any other detectable moiety (e.g., a detectable label or probe, such as one that is calorimetric, fluorescent, chemiluminescent, radioactive or magnetic). In a preferred embodiment, the anti-TAFIa or anti-TAFIai antibody is conjugated to horse-radish peroxidase (HRP). In another embodiment, the anti-TAFIa or anti-TAFIai antibody is conjugated to alkaline phosphatase.

In a still further embodiment, the assay comprises the use of a substrate for detectable label attached to the agent capable of binding to or being bound by the TAFIa or TAFIai/PTCI complex. In a particular embodiment the substrate is chromogenic, fluorescent, chemiluminescent or radioactive. In one embodiment, the substrate is 3,3',5,5'-tetramethylbenzidine (TMB). In another embodiment, the substrate is 3,3'-diaminobenzidine (DAB). In another embodiment, the substrate is 4-chloro-1-naphthol. In another embodiment, the substrate is o-phenylene-diamine (OPD). In another embodiment, the substrate is 3-amino-9-ethylcarbazole (AEC). In another embodiment, the substrate is fluorescent (e.g., Amplex Red).

In the assays described above, there are well known detection methods depending upon the assay format chosen. For example, ELISA plate readers are well known in the art for these types of immunoassays. Spectrophotometers and fluorometers are well known and useful for assays with a chromogenic or fluorescent probe. Liquid scintillation counters are well known and useful for assays employing a radioactive probe.

In one embodiment, the assay has a lower limit of detection of 0.1 µg/mL, preferably 0.02 µg/mL, more preferably 0.002 µg/mL and most preferably 0.001 µg/mL of TAFIa or TAFIai.

5.1.1 TAFIa/TAFIai Specific ELISA-Like Assay

In a preferred embodiment, the present invention is directed to an enzyme linked immunosorbent (ELISA)-like assay useful in measuring TAFIa and TAFIai (or a derivative or variant thereof) levels in solutions which may or may not contain the 60 kD proenzyme form of TAFI or the N-terminal activation peptide of TAFI. The assay is useful for diagnostic purposes related to the measurement of TAFIa and TAFIai (or a derivative or variant thereof) levels in a solution which may or may not contain the 60 kD proenzyme form of TAFI or the N-terminal activation peptide of TAFI.

The ELISA-like assay according to the present invention is an assay that utilizes a moiety capable of specifically binding to or being specifically bound by TAFIa and/or TAFIai. In certain embodiments, the moiety capable of specifically binding to or being specifically bound by TAFIa and/or TAFIai is a low molecular weight inhibitor, a small protein, plasminogen or a TAFIa or TAFIai specific antibody (i.e., binds to TAFIa or TAFIai but does not specifically bind to the 60 kD proenzyme form of TAFI or the N-terminal activation peptide of TAFI).

In a preferred embodiment, the moiety capable of specifically binding to or being specifically bound by TAFIa and/or TAFIai is the TAFI inhibitor PTCI. Preferably, PTCI is used as an immobilized binding agent to which TAFIa and/or TAFIai specifically bind in a sample.

In one embodiment, the assay comprises coating a solid support (e.g., a microtiter plate, a microwell strip, a bead or a microparticle) with PTCI followed by exposure of the PTCI coated solid support to a sample to determine TAFIa or TAFIai levels in the sample. Only TAFIa and TAFIai will bind to the immobilized PTCI and be detected in the sample. Preferably, there is a washing step at this point of the assay protocol to remove unbound forms of TAFI. The PTCI coated solid support is subsequently exposed to an agent capable of binding to or being bound by TAFIa or TAFIai (e.g., an anti-TAFIa or anti-TAFIai antibody, preferably conjugated to a detectable label, such as, for example horse-radish peroxidase (HRP)), but is not necessarily TAFIa or TAPIai specific (i.e., can bind the 60 kD proenzyme form of TAFI, such as Imuclone TAFI 873 by American Diagnostica, Inc.). Finally, a substrate (preferably of HRP, e.g., tetramethylbenzidine (TMB)) is added to detect the presence of the anti-TAFIa or anti-TAFIai agent.

In another embodiment, the assay comprises coating a solid support (e.g., a microtiter plate, a microwell strip, a bead or a microparticle) with PTCI followed by exposure of the PTCI coated solid support to a sample to determine TAFIa or TAFIai levels in the sample. Only TAFIa and TAFIai will bind to the immobilized PTCI and be detected in the sample. Preferably, there is a washing step at this point of the assay protocol to remove unbound forms of TAFI. The PTCI coated solid support is subsequently exposed to an agent capable of binding to or being bound by TAFIa or TAFIai (e.g., an anti-TAFIa or anti-TAFIai antibody, in one embodiment a monoclonal antibody, in another embodiment a human monoclonal antibody, in yet another embodiment AHTAFI-5024 or AHTAFI-5026), but is not necessarily TAFIa or TAFIai specific (i.e., can bind the 60 kD proenzyme form of TAFI, such as Imuclone TAFI 873 by American Diagnostica, Inc.). This step is preferably followed by a washing step and then the addition of a second antibody having a detectable label, such as an anti-mouse-HRP labeled conjugate (e.g., donkey anti-mouse-IgG-HRP conjugate). Finally, a substrate (preferably of HRP, e.g., tetramethylbenzidine (TMB)) is added to detect the presence of the anti-TAFIa or anti-TAFIai agent.

Addition of TMB substrate results in the production of a chromogenic product (blue) which turns yellow upon quenching of the reaction with sulfuric acid. The absorbance of the solution is measured at 450 nm and is directly proportional to the amount of TAFIa/TAFIai present in the solution.

In a preferred embodiment, the ELISA-like assay measures the level of TAFIa and TAFIai in a solution. Preferably, the assay is used to measure the level of TAFIa and TAFIai in a biological solution (e.g., blood, plasma, urine, serum, semen, sputum and cerebral or spinal fluid). The assay may also be used to quantify TAFIa and TAFIai levels in tissue samples as well as purified enzymatic systems and cell culture fluids.

In one embodiment, the assay comprises the TAFI inhibitor PTCI; a TAFIa standard; anti-human TAFI-HRP immunoconjugate; a chromogenic substrate of HRP, such as OPD or TMB; an appropriate buffer, e.g., 200 mM Tris-HCl, pH 7.4 buffer; and a quenching reagent, e.g., 0.45M $H_2SO_4$.

In another embodiment, the assay comprises the TAFI inhibitor PTCI; a TAFIa standard; an anti-human TAFI monoclonal antibody (e.g., AHTAFI-5024 or AHTAFI-5026, commercially available from Haematological Technologies, Essex Junction, Conn.); donkey anti-mouse-IgG-HRP labelled conjugate (commercially available from Jackson Laboratories, Jackson, Me.); a chromogenic substrate of HRP, such as OPD or TMB; an appropriate buffer, e.g., 200 mM Tris-HCI, pH 7.4 buffer; and a quenching reagent, e.g., 0.45M $H_2SO_4$.

In yet another embodiment, the anti-human TAFI monoclonal antibody is present in a concentration ranging from about 0.25 μg/mL to about 1.0 μg/mL. In yet another preferred embodiment, the donkey anti-mouse-IgG-HRP labeled conjugate is used at about a 1:1000 to about a 1:5000 dilution in an appropriate buffer (e.g., 200 mM Tris-HCl, pH 7.4 buffer).

In one embodiment, the assay according to the present invention utilizes small volumes of solution (about 25 μL) in total reaction volumes of about 250 μL, which makes reading the assay ideal for use with conventional 96-well microtest plate readers. In another embodiment, the assay according to the present invention can also be easily adapted to larger volumes (about 1 mL) of solution for reading in standard-sized cuvettes in conventional bench-top spectrophotometers. In another embodiment, the assay according to the present invention can be easily adapted to smaller volumes (less than 25 μL) for reading in high-throughput screening applications. The assay according to the present invention is fairly rapid, with the total assay time being between 30 and 60 minutes.

5.2 Diagnostic Methods

The present invention is also directed to a method of assaying biological solutions such as, but not limited to, blood, plasma, urine, serum, semen and cerebral or spinal fluid of a patient specifically for TAFIa or TAFIai (or derivatives or variants thereof) levels. The assay can be used to diagnose a particular disease or disorder or to monitor a subject that has been previously diagnosed with a particular disease or disorder. The assay can be further used to monitor a subject receiving treatment for a particular disease or disorder. In certain embodiments, the disease or disorder is any such disease or disorder associated with hyperfibrinolysis. In one embodiment, the disease or disorder is caused by hyperfibrinolysis. In another embodiment, hyperfibrinolysis is caused by the disease or disorder.

The result of the diagnostic assay can interpreted by comparison to controls or in relation to a parameter established through statistical analysis of previous assay results. In one embodiment, the quantity of TAFIa/TAFIai in a sample from a subject is compared to that from a subject(s) known not to have a particular disease or disorder (see e.g., Example 6.4). In another embodiment, the level (or range) of TAFIa/TAFIai in sample which is indicative of the presence or absence of a particular disease has been determined through statistical analysis of an adequate population of subjects. The determination of such a parameter can be accomplished by one of skill in the art using well known methods.

In one embodiment, the hemorrhagic disease or disorder includes, but is not limited to, hemophilia A, hemophilia B, autoimmune haemolytic anaemia, collagen diseases, von Willebrand disease (VWD), Henoch-Schonlein purpura, acute-generalized widespread bleeding, primary hyperfibrinolysis, hepatosplenic schistosomiasis, Factor deficiencies and hemostasis.

In another embodiment, the thrombotic disease or disorder includes, but is not limited to, heart attack, stroke, thromboembolic disease, acute myocardial infarction (AMI), deep vein thrombosis, acute ischemic stroke, massive pulmonary embolism, disseminated intravascular coagulation (DIC), anti-phospholipid syndrome, familial thrombophilia, thrombotic thrombocytopenic purpura sepsis, arthritis, fulminant hepatitis and thrombosis.

The hemorrhagic and thrombotic diseases and disorders occur, in part, because the normal balance between the coagulation and fibrinolytic cascades has been affected, altered or shifted. The methods of the present invention allow the shift of balance of the cascades to be detected, thus allowing for diagnosis or monitoring of treatment for hemorrhagic or thrombotic diseases or disorders.

In another embodiment, the hemorrhagic disease or disorder is a bleeding side-effect associated with the administration of tissue plasminogen activator (t-PA), urokinase plasminogen activator(u-PA), streptokinase, staphylokinase, plasminogen or analogs thereof, heparin, low molecular weight heparin, aspirin (e.g., overdose) or any other anticoagulant (e.g., overdose). In certain embodiments the bleeding side-effects include, but are not limited to, hemorrhagic transformation (HT).

In another embodiment, the disease or disorder is liver disease or acute or chronic cirrhosis.

In another embodiment, the disease or disorder is cancer, including but not limited to, breast cancer or leukemia.

In another embodiment, a surgical procedure is associated with the disease or disorder. In one embodiment, the surgical procedure is cardiovascular such as bypass surgery or aortic graft. In another embodiment, the surgical procedure is organ transplant. In specific embodiments, the organ transplant is liver transplant or heart transplant.

In another embodiment, the administration of TAFIa or stabilized TAFIa (or a derivative or variant thereof), an inhibitor of TAFIa, an activator of TAFIa or pharmaceutical composition thereof is associated with the disease or disorder.

5.2.1 Subject Population

In certain embodiments, the invention provides methods for quantifying levels of TAFIa and TAFIai (or derivatives or variants thereof) in a subject. The subject is preferably a mammal such as a non-primate (e.g., cows, pigs, horses, cats, dogs, mice, rats, etc.) or a primate (e.g., monkeys, such as cynomolgous monkeys, and humans). In a preferred embodiment, the subject is a human.

In one embodiment, the subject has or is susceptible to having a hemorrhagic and/or thrombotic disorder, or any other disease or disorder associated with aberrant levels of TAFIa or TAFIai, or a disease or disorder which can be treated, prevented or managed by modulation (e.g., increasing or decreasing) of TAFI, TAFIa or TAFIai activity.

In certain embodiments, the subject has or is susceptible to having a disease or disorder associated with a hyperfibrinolysis. In one embodiment, the disease or disorder is caused by hyperfibrinolysis. In another embodiment, hyperfibrinolysis is caused by the disease or disorder.

The invention also encompasses methods for quantifying levels of TAFIa and TAFIai (or derivatives or variants thereof) in a subject that is receiving or has received any treatment useful for the prevention or hemorrhagic and/or thrombotic diseases or disorders. In a preferred embodiment, the hemorrhagic and/or thrombotic disease or disorder, includes, but is not limited to, hemophilia A, hemophilia B, autoimmune haemolytic anaemia, collagen diseases, von Willebrand disease (VWD), Henoch-Schonlein purpura, acute-generalized widespread bleeding, primary hyperfibrinolysis, hepatosplenic schistosomiasis, Factor deficiencies, hemostasis, heart attack, stroke, thromboembolic disease, acute myocardial infarction (AMI), deep vein thrombosis, acute ischemic stroke, massive pulmonary embolism, disseminated intravascular coagulation (DIC), anti-phospholipid syndrome, familial thrombophilia, thrombotic thrombocytopenic purpura sepsis, arthritis, fulminant hepatitis and thrombosis, liver disease, acute or chronic liver cirrhosis, autoimmune haemolytic anaemia or any disease or disorder characterized by excessive bleeding or clotting.

In a preferred embodiment, the subject has or is susceptible to having hemophilia A or hemophilia B.

In another embodiment, the subject has or is susceptible to having cancer, including but not limited to, breast cancer or leukemia.

In another embodiment, the subject will be undergoing, is undergoing or has recently undergone a surgical procedure. In one embodiment, the surgical procedure is cardiovascular such as bypass surgery or aortic graft. In another embodiment, the surgical procedure is organ transplant. In specific embodiments, the organ transplant is liver transplant or heart transplant.

The assay can also be used to determine the levels of TAFIa or TAFIai (or derivatives or variants thereof) in a subject receiving conventional or experimental therapies that are used to prevent, treat or manage hemorrhagic and/or thrombotic diseases or disorders.

In one embodiment, the invention provides methods for quantifying levels of TAFIa or TAFIai in a subject currently undergoing alternative treatment for a hemorrhagic or thrombotic disease or disorder.

In another embodiment, the invention provides methods for quantifying levels of TAFIa or TAFIai in a subject who has previously undergone treatment for a hemorrhagic or thrombotic disease or disorder.

In another embodiment, the invention provides methods for quantifying levels of TAFIa or TAFIai in a subject who has never undergone treatment for a hemorrhagic or thrombotic disease or disorder.

In one embodiment, the treatment for the hemorrhagic disease or disorder is pro-coagulant therapy. In certain embodiments, the pro-coagulant therapy is the administration of amnino caproic acid, Factor VII, Factor VIII, Factor IX, Factor VIIa, Factor IXa, activated protein C, thrombin, fibrinogen or cryofractionalized plasma.

In one embodiment, the treatment for the thrombotic disorder is anti-coagulant therapy. In certain embodiments, the anti-coagulant therapy is plasminogen activator (t-PA), urokinase plasminogen activator(u-PA) or an analog thereof streptokinase, staphylokinase, plasminogen or analogs thereof, heparin, low molecular weight heparin or aspirin.

In another embodiment, the subject has been administered stabilized TAFIa (see U.S. patent application Ser. No. 10/116,095, filed Apr. 4, 2002, incorporated herein by reference), an inhibitor of TAFIa, or pharmaceutical composition thereof. In a particular embodiment, the stabilized TAFIa, inhibitor of TAFIa, or pharmaceutical composition thereof, was administered concurrently with one or more therapeutic or prophylactic agents in the same pharmaceutical composition. In another embodiment, the stabilized TAFIa, inhibitor of TAFIa, or pharmaceutical composition thereof was administered concurrently with one or more other therapeutic or prophylactic agents in separate pharmaceutical compositions. In certain embodiments, the other therapeutic or prophylactic agent is useful for the treatment, prevention or management of a hemorrhagic and/or thrombotic disorder. In other embodiments, the therapeutic or prophylactic agent is not useful for the treatment, prevention or management of a hemorrhagic and/or thrombotic disorder. In certain embodiments, the therapeutic or prophylactic agent includes, but is not limited to, t-PA, heparin, aspirin, Factor VII, Factor VIII, Factor IX, amino caproic acid, activated protein C, thrombin, fibrinogen, cryofractionalized plasma, actothrombin, low molecular weight heparin, hirudin, plasminogen, streptokinase, staphylokinase, urokinase or hirulong.

5.3 Kits

In one embodiment the invention provides an assay for specifically measuring TAFIa and/or TAFIai in a pack or kit comprising one or more containers filled with PTCI. In another embodiment, the pack or kit further comprises one or more containers filled with PTCI immobilized on a solid support. In another embodiment, the PTCI is free in a solution. In another embodiment, the PTCI is in powder form. In another embodiment, the PTCI is a lyophilized powder. In another embodiment, the PTCI is in a pro-PTCI form which is subsequently converted to active PTCI upon solvation (e.g., ester(s) of PTCI). In another embodiment, the pack or kit further comprises an agent that binds to the TAFIa/PTCI or TAFIai/PTCI complex and a means for detecting the bound agent. Further optionally associated with such container(s) can be instructions for use.

In another embodiment, the kit comprises microwell strips containing immobilized PTCI.

In another embodiment, the kit comprises a microtiter plate coated with immobilized PTCI. In another embodiment, the kit comprises beads coated with immobilized PTCI.

In another embodiment, the kit comprises a TAFIa or TAFIai standard, an agent that binds to or is bound by the TAFIa or TAFIai/PTCI complex, a buffer solution, a substrate of the agent that binds to or is bound by the TAFIa, or TAFIai/PTCI complex and a quenching agent. In one embodiment, the agent that binds to or is bound by the TAFIa or TAFIai/PTCI complex is anti-TAFIa or anti-TAFIai antibody conjugated to horseradish peroxidase (HRP).

In one embodiment, the substrate of the agent that binds to or is bound by TAFIa or TAFIai is TMB. In another embodiment, the substrate of the agent that binds to or is bound by TAFIa or TAFIai is OPD.

The invention further provides a pack or kit containing one or more buffers, substrates or developers, in one or more containers. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, the invention is directed to a kit comprising the components of the TAFIa/TAFIai ELISA assay. In a certain embodiment, the kit comprises microwell strips pre-coated with PTCI; a stabilized TAFIa standard; anti-human TAFI-HRP immunoconjugate; a chromogenic substrate of HRP, such as 0-phenylene diamine (OPD) or TMB; an appropriate buffer, e.g., 200 mM Tris-HCl, pH 7.4 buffer; and a quenching reagent, e.g., 0.45M $H_2SO_4$.

EXAMPLES

The following examples are offered by way of illustration, not limitation.

6.1 TAFIa/TAFIai Assay Protocol 6.1.1 Preparation of PTCI Coated Microtiter Plate A 2 μg/mL solution of PTCI is prepared by dissolving 1 mg of PTCI in 500 mL of 3-(N-morpholino)propanesulfonic acid (MOPs) buffer. 100 mL of the 2 μg/mL solution of PTCI is added to each well of the microtiter plate (e.g., an Immulon 4 (High Binding) 96-well microtiter plate) and incubated at 4° C. overnight in a moist chamber. The plate is then emptied and washed once with PBS/1% Tween buffer and 100 mL of blocking solution (e.g., SuperBloc, Pierce Chemicals, IN) is added to each well of the microtiter plate followed by incubation at room temperature for 20 minutes. The plates are then emptied, washed 2× with PBS/1% Tween buffer and air-dried.

6.1.2 Preparation of TAFIa/ai Standard

TAFIa/ai standard is prepared by adding TAFI, thrombin and thrombomodulin in buffer. The mixture is incubated at 37° C. for one hour. The TAFIa/ai can be stored frozen or lyophilized.

6.1.3 Preparation of anti-TAFI-HRP

500 μ/ml of anti-human TAFI monoclonal antibody is labeled with horseradish peroxidase (HRP) enzyme by known procedures (Kambegawa, *Nippon Rinsho* 53:2160-7 (1995). The anti-human TAFI-HRP immunoconjugate is diluted to 100 μg/mL in buffer and then diluted to 1 μg/mL in PBS/Tween buffer for use in the assay.

6.1.4 Assay Procedure

The assay for TAFIa, TAFIai, or a derivative or variant thereof can be performed either directly or indirectly.

For the direct assay, plasma is diluted 1:25 with 0.5% BSA/PBS/Tween buffer for use in the assay. Diluted test plasma is added to PTCI coated microwells (prepared as described above in section 6.1.1) and incubated at 37° C. for two hours. The plate is emptied and washed with PBS/Tween buffer. 100 mL of 1 mg/mL anti-human TAFI-HRP immunoconjugate (prepared as described above in section 6.1.2) is added to each well and incubated at 37° C.for one hour. The plate is emptied and washed 2X with PBS/Tween buffer. 100 mL of the HRP substrate TMB (Moss, PA) is added to each well and the color is allowed to develop for about 5 to about 15 minutes at room temperature. The reaction is stopped by the addition of 100 mL of 0.45M $H_2SO_4$. Absorbance is read at 450 nm.

For the indirect assay, plasma is diluted 1:25 with 0.5% BSA/PBS/Tween buffer for use in the assay. Diluted test plasma is added to PTCI coated microwells (prepared as described above in section 6.1.1) and incubated at 37° C. for two hours. The plate is emptied and washed with PBS/Tween buffer. 100 μL of 0.25-1.0 μg/mL anti-human TAFI monoclonal antibody (such as AHTAFI-5024 or AHTAFI-5026, commercially available from Haematological Technologies, Essex Junction, Vt.) is added to each well and incubated at 37° C. for one hour. The plate is emptied and washed 2× with PBS/Tween buffer. 100 μL of donkey anti-mouse IgG-HRP conjugate (commercially available from Jackson Laboratories, Jackson, Me.) is added and incubated at 37° C. for one hour. 100 mL of the HRP substrate TMB (Moss, Pa.) is added to each well and the color is allowed to develop for about 5 to about 15 minutes at room temperature. The reaction is stopped by the addition of 100 mL of 0.45M $H_2SO_4$. Absorbance is read at 450 nm.

6.1.5 TAFIa/ai Standard Curve

Figure 2:
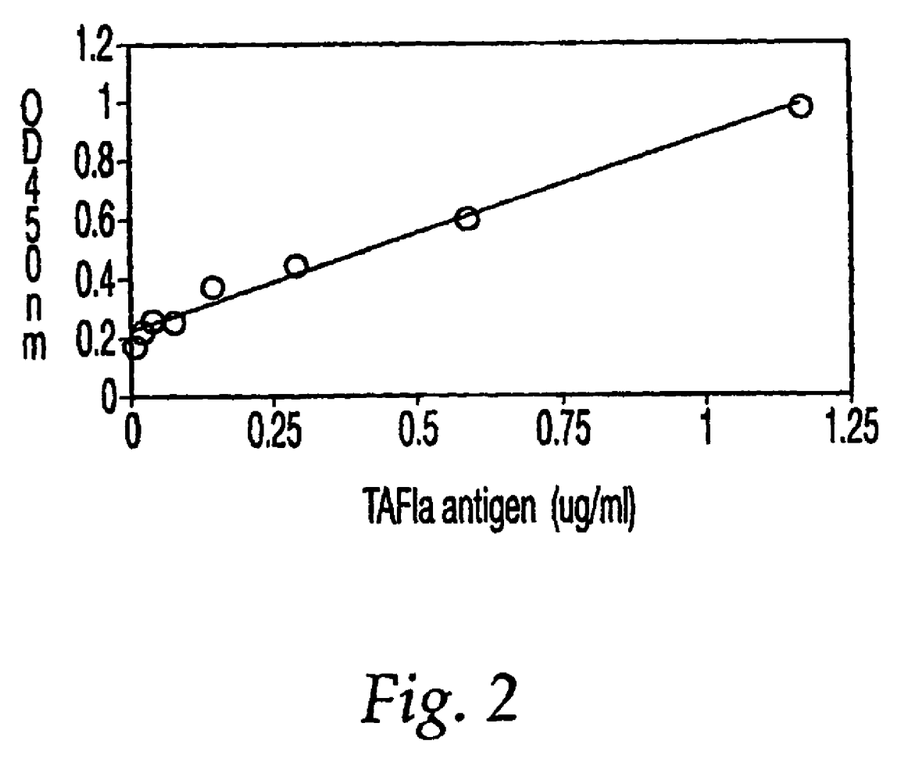
FIG. 2 shows a linear correlation between color development and TAFIa level in serially diluted standards.

The TAFIa/ai standard (prepared as described above in section 6.1.2) is serially diluted (1:2) starting at 1.25 μg/mL and applied to a PTCI-coated microtiter plate. The ELISA-like assay is then performed as described above in section 6.1.4. There is a linear correlation between color development and TAFIa/ai antigen (see FIG. 2).

6.2 Specificity of TAFIIa/TAFIai Assay in the Presence of TAFI

Figure 3:
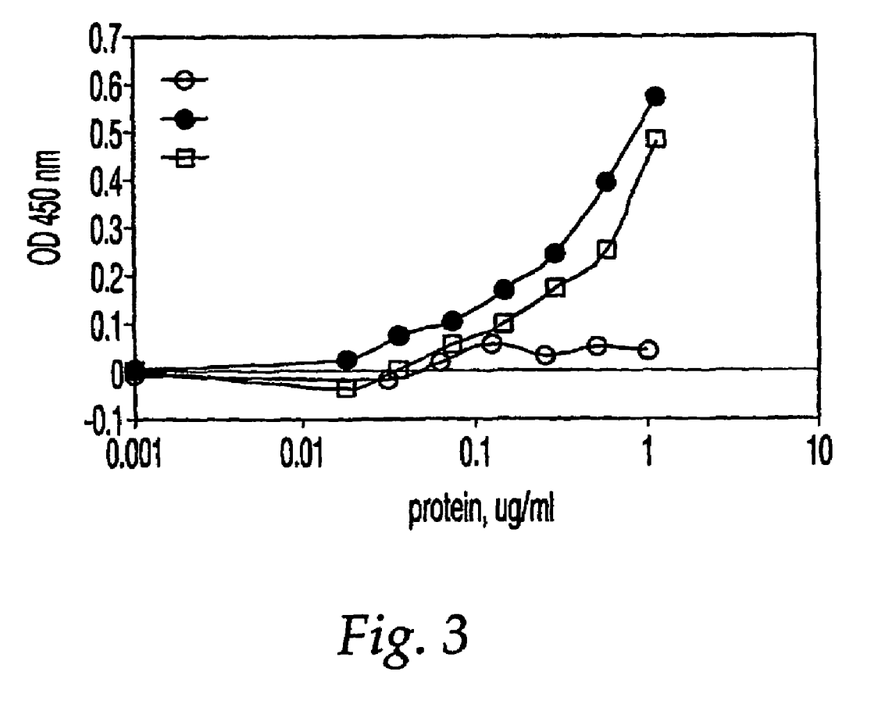
FIG. 3 shows the specificity of the ELISA assay for TAFIa and TAFIai in the presence of TAFI (60 kD proenzyme).

TAFIa was prepared by incubation of TAFI with thrombin/thrombomodulin. TAFIai was prepared as described above in section 6.1.2. Solutions containing TAFI, TAFIa and TAFIai (0.001-1 μg/mL) were tested in the ELISA-like assay as described above in section 6.1.4. The results as shown in FIG. 3 illustrate that the ELISA-like assay specifically measures TAFIa and TAFIai but not TAFI.

Figure 4:
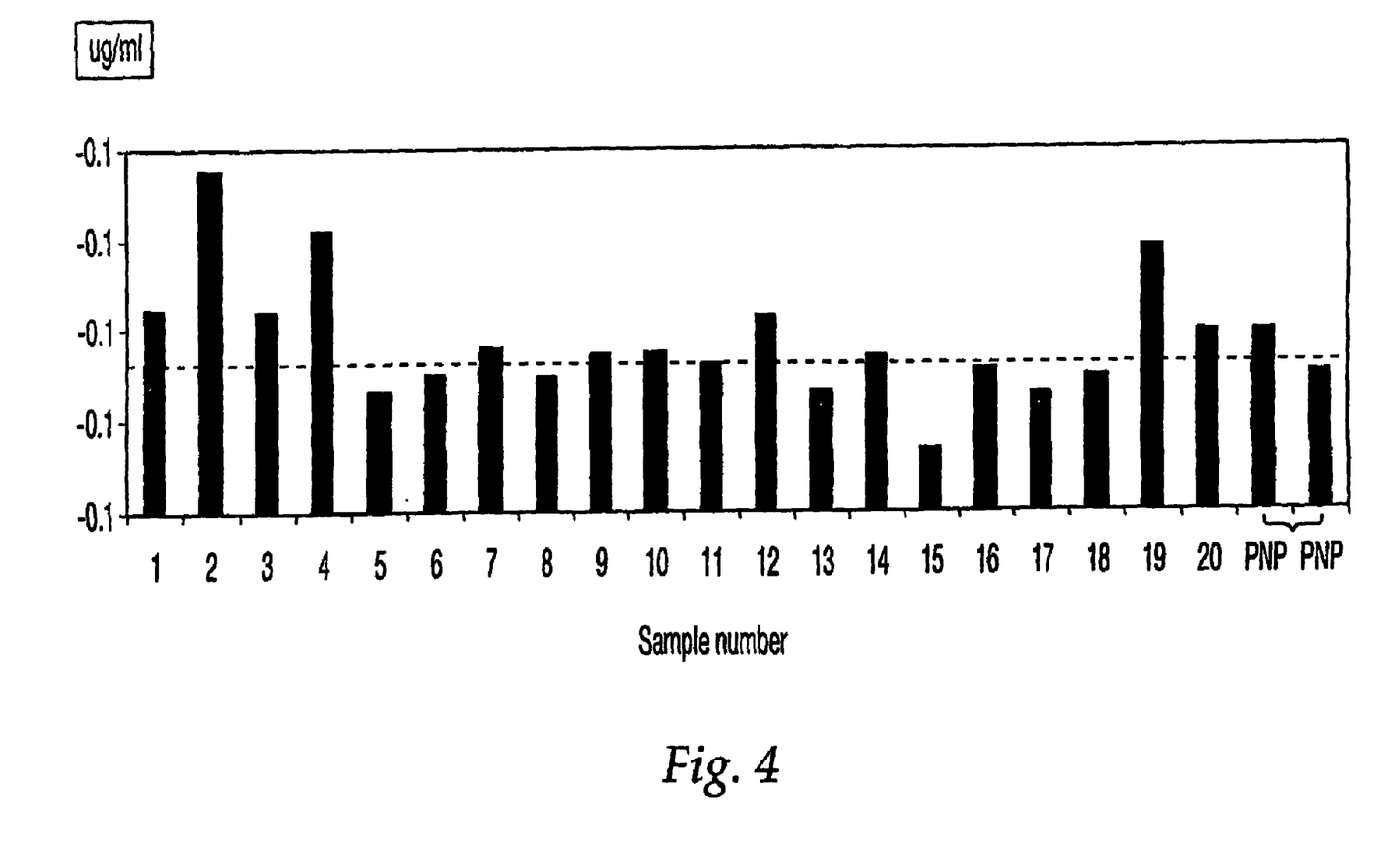
FIG. 4 illustrates the quantitation of TAFIa/TAFIai antigen in plasma from Pooled Normal Plasma (PNP) and hemophilia patients.

6.3 Quantitation of TAFIa/TAFIai in Plasma from Pooled Normal Plasma (PNP) and Hemophilia Patients Plasma samples from patients diagnosed with hemophilia A or hemophilia B (n=20) and from normal people (pooled normal plasma (PNP); n=2) were tested for the presence of TAFIa/ai antigen using the ELISA-like assay as described above in section 6.1.4. The results are illustrated in FIG. 4. The two PNP samples were determined to have 7-10 μg/mL TAFIa/TAFIai whereas the hemophilia plasma ranged from 3-17 μg/mL TAFIa/ai antigen. TAFIa/TAFIai levels were elevated above PNP levels in 12/20 hemophilia plasma samples. These results show that TAFIa/TAFIai levels are elevated in hemophilia serum and suggests that hemophilia patients are in a hyperfibrinolytic state.

Figure 5:
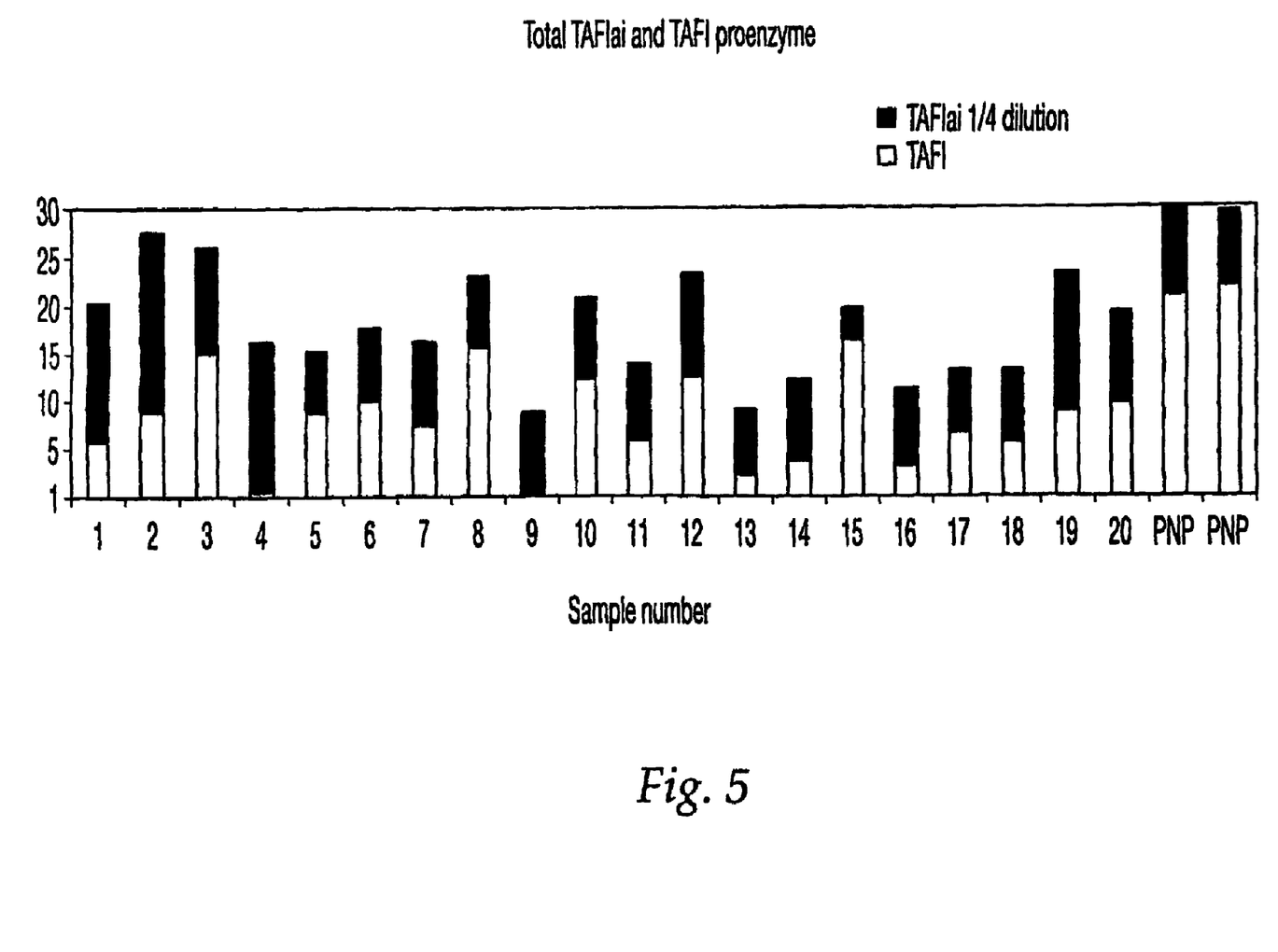
FIG. 5 shows the total TAFI (TAFI+TAFIa+TAFIai) levels in Pooled Normal Plasma (PNP) and hemophilia plasmas.

6.4 Quantitation of Total TAFI Protein (TAFI proenzyme+ TAFIa/TAFIai) Levels in Plasma from Pooled Normal Plasma (PNP) and Hemophilia Patients Plasma samples from patients diagnosed with hemophilia A or hemophilia B (n=20) and from normal people (pooled normal plasma (PNP); n=2) were tested for the level of TAFI proenzyme using a functional chromogenic assay (Actichrome 874 by American Diagnostica, Inc.). The total amount of TAFI protein in each plasma sample (TAFI proenzyme+TAFIa/TAFIai) was then calculated using the TAFIa/ai data from Example 6.3 and results from the Actichrome TAFI assay. The results are illustrated in FIG. 5. The total TAFI level in PNP (mean =28 μg/mL) was significantly greater than the total TAFI level in all of the hemophilia serum samples (mean=16.9 μ/mL). These results show that TAFI levels in hemophilia serum samples are significantly reduced and suggests that TAFI is more readily metabolized in hemophilia serum.

6.5 Percentage of Total TAFI Protein Contributed to by TAFIa/TAFIai Antigen

Figure 6:
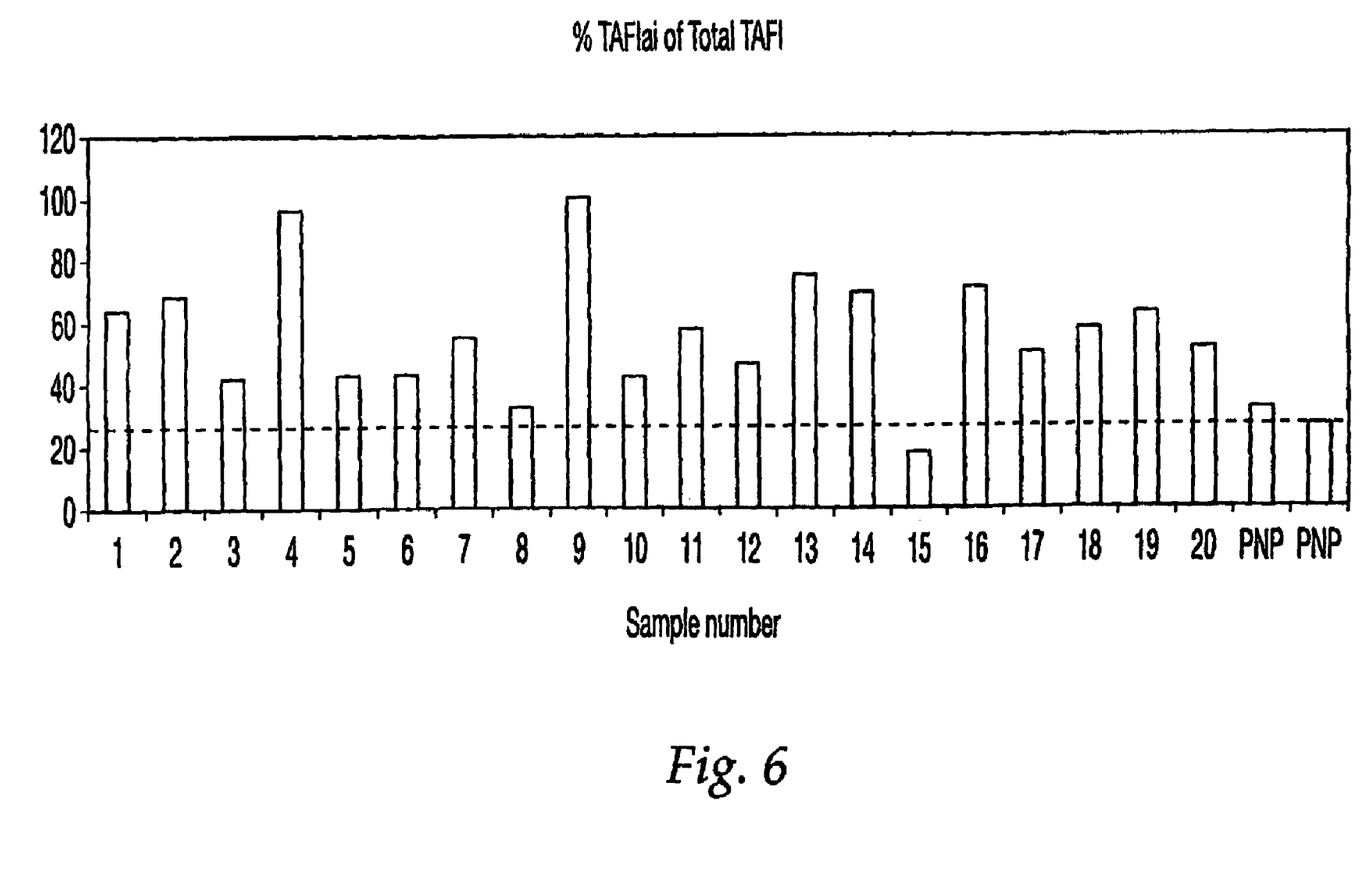
FIG. 6 shows the percentage of total TAFI (TAFI+TAFIa+TAFIai) level contributed to by TAFIa and TAFIai in Pooled Normal Plasma (PNP) and hemophilia plasmas.

The percentage of total TAFI protein that is represented by TAFIa/TAFIai antigen that is present in plasma samples from patients diagnosed with hemophilia A or hemophilia B (n=20) and from normal people (pooled normal plasma (PNP); n=2) was calculated using the date from Examples 6.3 and 6.4. The results are illustrated in FIG. 6. TAFIa/TAFIai antigen represents about 25% of the total TAFI present in PNP, whereas TAFIa/TAFIai antigen represents greater than 50% of the total TAFI present in hemophilia serum. In 18/20 of the hemophilia serum samples, the percentage of total TAFI contributed to by TAFIa/TAFIai antigen was significantly greater than in the PNP samples. This indicates that the percentage of total TAFI that is contributed to by TAFIa/TAFIai antigen may be a useful marker for diagnosis and/or monitoring of hemophilia.

What is claimed is:

1. A method for detecting active thrombin activatable fibrinolytic inhibitor (TAFIa) or inactive thrombin activatable fibrinolytic inhibitor (TAFIai), but not a 60 kD proenzyme form of thrombin activatable fibrinolytic inhibitor (TAFI) or a N-terminal activation peptide of TAFI, in a sample, said method comprising:
   (i) contacting said sample with a potato carboxypeptidase inhibitor (PTCI) under conditions that permit binding of PTCI to TAFIa or TAFIai; and
   (ii) detecting the presence of a TAFIa/PTCI complex or a TAFIai/PTCI complex,
   wherein the TAFIa, or TAFIai or PTCI is immobilized on a solid support.

2. The method of claim 1, wherein potato carboxypeptidase inhibitor (PTCI) is immobilized onto a solid support.

3. The method of claim 2, wherein the solid support is a microtiter plate.

4. The method of claim 2, wherein the solid support is a bead or microparticle.

5. The method of claim 1, wherein said detecting step further comprises contacting said sample with an agent which binds to the TAFIa or TAFIai region of the TAFIa/PTCI complex or the TAFIai/PTCI complex.

6. The method of claim 5, wherein said agent is an anti-TAFIa or anti-TAFIai antibody conjugated to horseradish peroxidase (HRP).

7. The method of claim 5, wherein said agent is an anti-TAFIa or anti-TAFIai monoclonal antibody.

8. The method of claim 7, wherein said detecting step comprises contacting said sample with an agent that binds to the anti-TAFIa or anti-TAFIai monoclonal antibody, said agent being conjugated to HRP.

9. The method of claim 8, wherein said agent is donkey anti-mouse-IgG-HRP.

10. The method of claim 6 or 9, wherein said detecting step comprises contacting said sample with a substrate of horseradish peroxidase (HRP).

11. The method of claim 10, wherein said horseradish peroxidase (HRP) substrate is 3,3',5,5'-tetramethylbenzidine (TMB).

12. The method of claim 1, wherein the sample is a biological fluid from a patient.

13. The method of claim 12, wherein the biological fluid is plasma.

14. The method of claim 12, wherein the biological fluid is blood, urine, serum, semen or cerebral or spinal fluid.

15. The method of claim 12, wherein the patient has a thrombotic disorder.

16. A method of claim 15, wherein the thrombotic disorder is heart attack, stroke, thromboembolic disease, acute myocardial infarction (AMI), deep vein thrombosis, acute ischemic stroke, massive pulmonary embolism, disseminated intravascular coagulation (DIC), anti-phospholipid syndrome, familial thrombophilia, thrombotic thrombocytopenic purpura sepsis, arthritis, fulminant hepatitis or thrombosis.

17. The method of claim 12, wherein the patient has a hemorrhagic disorder.

18. The method of claim 17, wherein the hemorrhagic disorder is hemophilia A, hemophilia B, autoimmune haemolytic anaemia, a collagen disease, von Willebrand disease (VWD), Henoch-Schonlein purpura, acute-generalized widespread bleeding, primary hyperfibrinolysis, hepatosplenic schistosomiasis, or hemostasis.

19. The method of claim 12, wherein the patient is undergoing anti-coagulant therapy.

20. The method of claim 19, wherein the anti-coagulant therapy is administration of tissue plasminogen activator (t-PA), or urokinase plasminogen activator(u-PA).

21. The method of claim 19, wherein said anti-coagulant therapy is administration of aspirin.

22. The method of claim 19, wherein said anti-coagulant therapy is administration of streptokinase, staphylokinase, plasminogen, heparin or low molecular weight heparin.

23. The method of claim 12, wherein the patient is undergoing procoagulant therapy.

24. The method of claim 23, wherein the procoagulant therapy is administration of amino caproic acid, Factor VII, Factor VIII, Factor IX, Factor VIIa, Factor IXa, activated protein C, thrombin, fibrinogen or cryofractionalized plasma.

25. The method of claim 12, wherein the patient is susceptible to having a thrombotic disorder.

26. The method of claim 25, wherein the thrombotic disorder is heart attack, stroke, thromboembolic disease, acute myocardial infarction (AMI), deep vein thrombosis, acute ischemic stroke, massive pulmonary embolism, disseminated intravascular coagulation (DIC), anti-phospholipid syndrome, familial thrombophilia, thrombotic thrombocytopenic purpura sepsis, arthritis, fulminant hepatitis or thrombosis.

27. The method of claim 12, wherein the patient is susceptible to having a hemorrhagic disorder.

28. The method of claim 27, wherein the hemorrhagic disorder is hemophilia A, hemophilia B, autoimmune haemolytic anaemia, collagen diseases, von Willebrand disease (VWD), Henoch-Schonlein purpura, acute-generalized widespread bleeding, primary hyperfibrinolysis, hepatosplenic schistosomiasis, or hemostasis.

29. The method of claim 1, wherein the lower limit of detection of TAFIa and TAFIai in the solution is about 0.1 µg/mL.

30. The method of claim 1, wherein the lower limit of detection of TAFIa and TAFIai in the solution is about 0.02 µg/mL.

31. The method of claim 1, wherein the lower limit of detection of TAFIa and TAFIai in the solution is about 0.002 µg/mL.

32. The method of claim 1, wherein the lower limit of detection of TAFIa and TAFIai in the solution is about 0.001 µg/mL.

* * * * *